United States Patent [19]

Bunger

[11] Patent Number: 5,714,515
[45] Date of Patent: Feb. 3, 1998

[54] PHARMACEUTICAL ALPHA-KETO CARBOXYLIC ACID COMPOSITIONS, METHOD OF MAKING AND USE THEREOF

[75] Inventor: Rolf Bunger, McLean, Va.

[73] Assignee: The United States of America as represented by the Secretary of the Army, Washington, D.C.

[21] Appl. No.: 646,572

[22] Filed: May 8, 1996

Related U.S. Application Data

[62] Division of Ser. No. 239,635, May 9, 1994, Pat. No. 5,536,751.

[51] Int. Cl.$^6$ .............. A61K 31/19; A61K 31/20
[52] U.S. Cl. .............. 514/557; 426/103; 426/556; 426/590; 426/660; 514/558; 514/559; 514/560
[58] Field of Search .............. 514/557, 558, 514/559, 560; 562/577; 554/1, 220, 221, 223; 426/556, 590, 103, 660

[56] References Cited

U.S. PATENT DOCUMENTS

| | | | |
|---|---|---|---|
| 4,507,319 | 3/1985 | Barratt et al. | 514/546 |
| 4,824,865 | 4/1989 | Bowser et al. | 514/558 |
| 5,091,171 | 2/1992 | Yu et al. | 424/546 |

OTHER PUBLICATIONS

Mallet et.al., 8th heavy Goldberg Workshop, pp. 1–9, 1992.
Nohl et.al., Free Rad. Res. Com., 18(3), pp. 127–133, 1993.
Downey, Annu., Rev. Physio., 52, pp. 487–504, 1990.
Paller et.al., J. Clini. Invest., 1156–1164, 1984.
Camporti, Lab Invest.,53(6), 599–623, 1985.
Salahudeen et.al., J. Clin. Invest, vol. 88, 1886–1893, 1991.
Nicotera et.al., Drug. Metab. Rev., 20(2–4) 193–201, 1989.
Cohen, Handbook of method fpr oxygen radical research, 55–64, 1985.
Funk et.al., Eur. J. Biochem, 152, 167–172, 1985.
Voogd et.al., J.Clinic Invest., 1995.
Reed, Annu. Rev. Pharmac. Toxic., 30:603–31, 1990.
Zimmer et.al., J. Mol. and Cell. Card., 531–535, 1981.
Duhm., Biochim. Biophysic. Acta, 89–100, 1974.
Holroyde et.al., Biochem. Biophysic. Acta, 63–69, 1979.
Kusoaka et.al., Circulation Research, 66, No. 5, 1990.
Hofmann et.al., Circulation Reasearch, vol. 72, No. 1, 1993.
Bunger et.al., Pflugers Arch., 397:214–219, 1983.

*Primary Examiner*—Shailendra Kumar
*Attorney, Agent, or Firm*—Werten F. W. Bellamy

[57] ABSTRACT

A pharmaceutical composition comprising as an active phosphorylation potential enhancing substance and an alpha-keto carboxylic acid or a pharmaceutically-acceptable salt thereof, its use and products containing the same.

8 Claims, No Drawings

PHARMACEUTICAL ALPHA-KETO CARBOXYLIC ACID COMPOSITIONS, METHOD OF MAKING AND USE THEREOF

This is a division of application Ser. No. 08/239,635, filed May 9, 1994, now U.S. Pat. No. 5,536,751. +gi

GOVERNMENT INTEREST

This Invention described herein may be manufactured, licensed and used by or for the U.S. Government without the payment of any royalties to us thereon. The Federal Government has a nonexclusive nontransferable, irrevocable, paid-up license to practice or have practiced for or on behalf of the U.S. any subject invention throughout the world.

TECHNICAL FIELD OF THE INVENTION

The invention is in the field of protecting, preserving and restoring normal cell functions. More specifically it is in the field of using alpha-keto carboxylic acid compositions as prophylactic and therapeutic agents to prevent the deterioration or promote the restoration and preservation of normal cell functions.

BACKGROUND OF THE INVENTION

Pyruvate is the key glycolytic intermediate of all mammalian cells. As discussed in more detail below, this substance and pharmaceutically acceptable derivatives thereof are useful as biological stimulating agents.

1) Pyruvate compartmentalization and cytoplasmic phosphorylation potential: Intracellular pyruvate is usually derived from glucose, i.e. it is a key glycolytic intermediate of all mammalian cells. It can also be formed from extracellular lactate via the lactate dehydrogenase reaction. In situations where pyruvate is employed as an exogneous metabolic substrate, i.e. where its extracellular concentration is sufficiently raised, pyruvate functions as a precursor of lactate by reversing the lactate dehydrogenase reaction. Further, in contrast to alternative metabolic fuels such as acetate and also lactate, pyruvate has recently been established by applicant as an agent that consistently improves key indices of the cytoplasmic phosphorylation potential of creatine phosphate (ratios of the concentrations of creatine phosphate (CrP) to inorganic phosphate ($P_i$), to that of creatine (Cr), or to the product of the concentrations of creatine and inorganic phosphate, [CrP]/([Cr]*[Pi]); a formally similar concentration ratio is the phosphorylation potential of ATP, [ATP]/([ADP]*[$P_i$]), which is coupled to and in most cases in equilibrium with [CrP]/([Cr]*[$P_i$]), an effect mediated by the powerful magnesium- and pH- dependent enzyme creatine kinase; this enzyme is present in high concentrations in striated and smooth muscle (heart, vascular smooth muscle, skeletal muscle) and brain, but not in liver and kidney. [ATP]/([ADP]*[$P_i$]) is a major determinant of the actual free energy available from cellular ATP hydrolysis according to the following equation:

$$\Delta G_{ATP} = \Delta G^{o}_{ATP} + R \cdot T \cdot \ln([ADP] \cdot [P_i]/[ATP])$$

in which $\Delta G^{o}_{ATP}$ is the (relatively constant) standard free energy change of ATP hydrolysis under conditions prevailing in vivo (−32.35 kJ/mol, pH 7.2, free cytoplasmic magnesium concentration <1 mM), R=gas constant (8.314 J/K*mol) and T=absolute temperature in degrees Kelvin (K). Thus, during alterations of physiologic states and under many pathophysiological states investigated so far, [ATP]/([ADP]*[$P_i$]) can change considerably, whereas the $\Delta G^{o}_{ATP}$ term changes relatively little.

Pyruvate, administered in doses between 2 to 10 mM, has recently been demonstrated by applicant to raise the phosphorylation potential in a dose-dependent manner in normal, but especially in reversibly damaged (ischemia/reperfusion protocols) heart models of guinea pig, dog and pig. Thus, pyruvate administration can somewhat (by about 4 to 6%) improve the free energy available for cellular phosphorylations and energy consuming ion transporters as well.

Pyruvate is centered at the compartmental interface between cytoplasma and mitochondria; applicant has recently shown that it is linked via the cytoplasmic $NAD^+$/NADH system (which is under the joint control of two major cytoplasmic dehydrogenases, the lactate dehydrogenase and the glyceraldehyde-3-phosphate dehydrogenase) to the cytoplasmic phosphorylation potential. Thus, pyruvate is coupled to [ATP]/([ADP]*[$P_i$]) in its capacity as substrate of lactate dehydrogenase, which can affect the $NAD^+$/NADH system which in turn is stoichiometrically coupled the combined glyceraldehyde-3-phosphate dehydrogenase/3-phosphoglycerate kinase reaction; the latter enzyme system involves ATP, ADP, and $P_i$ as reactants, i.e. is linked directly to the cytoplasmic [ATP]/([ADP]*[$P_i$]) rather than the CrP phosphorylation potential, [CrP]/([Cr]*[$P_i$]). In practice, [ATP]/([ADP]*[$P_i$]) is usually determined using the [CrP]/([Cr]*[$P_i$]), but applicant has demonstrated that it also can be estimated using the reactants of the glyceradehyde-3-phosphate dehydrogenase combined with those of the lactate dehydrogenase.

2) Pyruvate dehydrogenase: Pyruvate is also the immediate substrate of the powerful mitochondrial pyruvate dehydrogenase enzyme complex (PDH), the main mechanism that controls entry of carbohydrate and lactate carbon into the citric acid cycle for end-oxidation (formation of water and carbon dioxide) coupled with oxidative phosphorylation (formation of ATP from ADP and inorganic phosphate). In addition, pyruvate, not lactate or acetate, is autocatalytically active at the PDH enzyme complex; thus pyruvate stimulates covalent modification (dephosphorylation) of the interconvertible PDH complex, which results in increased activity of the PDH; this in turn stimulates oxidative decarboxylation of pyruvate to acetyl-CoA and carbon dioxide and hence facilitates complete conversion of cellular glucose- and lactate-carbon to water and carbon dioxide (see below). The net effect of these changes is an increased availability of NADH in the mitochondria, thereby improving the ability of the cell to adapt promptly to changing energy demands.

3) Pyruvate Carboxylase: Another important feature of pyruvate only (not of other substrates such as lactate or acetate), is that it functions as the immediate substrate of the $CO_2$-fixing-enzyme pyruvate carboxylase. This enzyme is present in relatively small amounts in liver and heart and probably other organs as well; but it is important, since it assimilates metabolic $CO_2$ by adding it to the carbon-3-skeleton of pyruvate, thus providing the mammalian cell with an "anaplerotic" mechanism; the overall effect is the netsynthesis of mitochondrial carbon-4-skeletons, which helps to adequately maintain the concentration of the rather small but absolutely vital carbon-4-oxaloacetate pool in the mitochondria. Oxaloacetate is crucial for the mitochondrial condensing enzyme (citrate synthase) which catalyzes the aldol condensation between the methyl group of acetyl-CoA (generated in the PDH reaction or derived from ketone body or fatty acid metabolic pathways) and the carbonyl group of oxaloacetate resulting in the formation of citrate and coenzyme A. Oxaloacetate, an alpha-ketoacid like pyruvate and alpha-ketoglutarate, is normally present in the mitochondrial matrix in only very small concentrations; it is clear therefore that maintenance of its mitochondrial concentration can become crucial for adequate citric acid cycle turnover, the mechanism which provides the necessary reducing equivalents ($NADH_2$, $FADH_2$) for the respiratory chain which in turn ensures maintenance of ATP synthesis (oxidative phosphorylation) and hence cellular energy status (phosphorylation potential).

4) Lactate dehydrogenase and cytoplasmic $NADH_2$: At physiological pH of 7.0 to 7.4 pyruvic acid, because of its relatively low pK value of 2.49, is virtually completely dissociated into the negatively charged pyruvate anion and the positively charged $H^+$ cation. It is known that the pyruvate anion (but probably also the undissociated free pyruvic acid), if administered in sufficient quantities, lowers the cytoplasmic $[NADH]*[H^+]/[NAD^+]$ ratio in cellular systems that contain lactate dehydrogenase. This effect is often referred to as the oxidizing effect of pyruvate. It has been recently demonstrated by applicant that this effect of pyruvate can prevent the normal accumulation of cytoplasmic $NADH_2$ during experimental cardiac ischemia [1]. This special oxidizing mechanism of pyruvate is potentially of great clinical significance, as extramitochondrial $NADH_2$ has been found by others to be hazardous for isolated heart mitochondria (not for isolated liver mitochondria); in isolated heart mitochondria $NADH_2$ lowers respiratory control and impairs energy coupling (ATP/oxygen ratio decreases) during readmission of oxygen; simultaneously the anoxic/ reoxygenated $NADH_2$-exposed cardiac mitochondria begin to double the generation of the pathological superoxide anion ($O_2$—) [2]; the superoxide anion belongs to a special class of reactive oxygen species usually called oxygen-derived free radicals; these molecular species have been implicated in the pathogenesis of oxidative stress during ischemia/reperfusion conditions of several organs such as heart, kidney and liver [3–6]. Both the impairment of energy coupling and the pathological superoxide anion formation were only observed when the isolated heart mitochondria were incubated with $NADH_2$, not during acidosis or anoxia per se, i.e. in the absence of $NADH_2$. Considering these new findings from isolated cardiac mitochondria, the recent demonstration by applicant that pyruvate can prevent large accumulations of $NADH_2$ during ischemia [1], it becomes evident that pyruvate—via its oxydizing effect per se—could be instrumental could be instrumental in maintaining adequate mitochondrial energy coupling during subsequent reperfusion. According to the above rationale this would additionally be associated with a lower production rate of potentially dangerous oxygen-derived free radicals (superoxide anions). It is readily seen that these redox-effects of pyruvate may lead to improved reperfusion energetics and hence functional recovery in any organ that contains sufficient amounts of lactate dehydrogenase. As for the heart, anticipated improvements include reduced myocardial stunning, reduced probability of arrhythmias and ventricular fibrillation, reduced accumulation of sodium and hence calcium; attenuation of cytoplasmic calcium accumulation is particularly important, since unphysiologically high concentrations of the calcium ion can activate dangerous autolyric enzymes such as phospholipases (membrane lipid damage), proteases (cytoskeletal protein and enzyme damage), and endonucleases (DNA strand breaks [7]).

5) Fenton reaction, $Fe^{2+}$ (ferrous Ion) and reducing equivalents: There is yet another reason why the cytoplasmic redox effects of high concentrations of pyruvate could be beneficial during ischemia-acidosis/reperfusion situations; this mechanism concerns the formation of cytotoxic oxygen-derived free radicals via Fenton-type reactions. This is the case because the Fenton reaction is the mechanism responsible for generation of the particularly cytotoxic hydroxyl radical; the reaction requires catalytic amounts of free $Fe^{2+}$ (ferrous Ion) which interacts with hydrogen peroxide or the superoxide anion to yield three products: $Fe^{3+}$ plus hydroxyl ion (both relatively inert) and the extremely reactive and therefore cytotoxic hydroxyl radical [8]. Normally most of cellular iron is complexed in the form of $Fe^{3+}$ by ferritin or stored as haem-type-iron in proteins, enzymes, and cofactors. These complexes usually contain iron but are not themselves substrates or catalysts in Fenton-type reactions. However, during accumulation of reducing equivalents ($FADH_2$ $FMN_2$, $NADH_2$) in ischemic/anoxic/infarcted organs, reduced flavins can bring about the reductive release of iron from ferritin [9]; this raises the concentration of free Fe2+ (ferrous Ion) which may then be available to react with hydrogen peroxide/superoxide anion of, e.g., mitochondrial origin during subsequent reperfusion. Indeed, during rat cardiac ischemia, accumulation of free $Fe^{2+}$ (ferrous Ion) has recently been demonstrated, especially when ischemia was associated with significant cellular acidosis [10]. Since pyruvate treatment can help to metabolically neutralize cellular $H^+$ (as opposed to direct chemical buffering by, e.g., bicarboante) and also has been shown by applicant to prevent accumulation of reducing equivalents during ischemia by "clamping" the cytoplasmic redox status at the normoxic level [1]. it is easily seen that acute parenteral pyruvate has the potential to attenuate or perhaps even completely prevent the intracellular reductive liberation of free $Fe^{2+}$ (ferrous ion) during acidotic ischemia/anoxia. Applicant proposes that this special redox-effect of pyruvate Has the potential to attenuate/prevent Intracellular Fenton-type reactions, which in turn would diminish or perhaps even completely eliminate the formation of the cytotoxic hydroxyl radical from hydrogen peroxide or superoxide anion. Consequently, oxidative stress due to reperfusion/ reoxygenation can be expected to be minimized, if adequate pyruvate therapy can be timely implemented to minimize the accumulation of reducing equivalents during pre-reperfusion ischemia/anoxia conditions. This particular and novel pyruvate mechanism will likely apply to all mammalian organs that contain lactate dehydrogenase and ferritin iron (e.g., brain, heart, kidney, lung); probable exceptions are liver and spleen since these organs do not appear to have substantial amounts of ferritin (for review see ref. [10]).

6) Intracellular hydrogen ion balance and metabolic removal of $H^+$: Applicant also proposes that pyruvate can also influence favorably the cellular hydrogen ion balance. Therapeutically applied pyruvate stimulates hydrogen ion removal by metabolic consumption as opposed to direct chemical buffering or neutralization as meditated by .e.g., bicarbonate or other cellular buffers; thus pyruvate can enhance metabolic removal (cause covalent sequestration of) intracellular hydrogen ions. Virtually all major mammalian cell types have at least four major enzymatic mechanisms at their disposal by which pyruvate metabolism contributes to this type of metabolic consumption of $H^+$: a) during reduction of pyruvate to lactate via lactate dehydrogenase one $H^+$ ion is consumed to form the lactate anion; lactate anion can then be washed out (transported across the cell membrane) by a specific process which comprises obligatory co-export with another $H^+$ ion ($H^+$-symport); this export system is the powerful monocarboxylate transport system of the cell membrane; b) during oxidative decarboxylation of pyruvate by pyruvate dehydrogenase, prior mitochondrial H⁺-import removes cytoplasmic H⁺, i.e. for one pyruvate decarboxylated one H⁺ ion is stoichiometrically consumed turning up ultimately in the water generated by the mitochondrial respiratory chain; c) during $CO_2$-fixation by maleate dehydrogenase (malic enzyme, decarboxylating $NADP^+$-dependent malate dehydrogenase) malate anion is formed and again one H⁺ ion is stoichiometrically consumed to form malate and $NADP^+$. d) Furthering the oxidative metabolism of pyruvate plus one. H⁺ is also the already mentioned anaplerotic pyruvate carboxylase of the mitochondria. Thus, the pyruvate anion functions as natural hydrogen ion remover, gently alkalinizing cells and blood without depending on external buffers like bicarbonate. Thus the applicant contends that pyruvate can possibly function as an alternative to traditional and perhaps less gentle treatments of metabolic acidosis by bicarbonate. The advantage of pyruvate cellular alkalization would be that systemic pyruvate application drives Hydrogen ions out of the cells, whereas bicarbonate drives hydrogen ion into the cells (exacerbating intracellular acidosis) until the excess $CO_2$ is eliminated via the lungs.

A moderate alkalization is desirable for all mammalian cells or organs that recover from damage associated with intracellular acidification; this would apply to situations where the residual metabolism has become acidotic and must be restarted to reestablish normal ion homeostasis simultaneous with replenishment of crucial cellular metabolite pools (especially that of mitochondrial oxaloacetate) and energy stores (phosphorylation potential). The potential for reductive release of hazardous free iron from cellular complexes (ferritin, myoglobin, cytochromes) will also be diminished by pyruvate, since Fe2+ (ferrous Ion) release under intracellular conditions requires the above described accumulation of reducing equivalents in combination with H⁺ (acidosis). Clearly, applicant can claim that pyruvate has the potential to influence favorably cellular redox and hydrogen ion balances, via its effects on the cytoplasmic $[NAD^+]/[NADH]*[H^+]$ ratio and its H⁺-consuming metabolic pathways; these features appear to be particularly efficacious in states of partial and reversible cell damage and/or recovery from damage or from extreme stress: reoxygenation after hypoxia, reperfusion after ischemia and myocardial infarct, reestablishing coronary circulation after cardiopulmonary bypass, reperfusion after percutaneous transluminal coronary angioplasty, reperfusion after enzymatic recanalization of thrombotic vessels (streptokinase-type interventions), recovery from excessive catecholamine stress or physical exertion, recovery from probably all types of circulatory shock, if they were associated with hypoxia/ischemia and acidosis.

7) Protection of essential —SH groups: If during cellular damage reductive release of free Fe2+ (ferrous Ion) occurred, triggering Fenton-type reactions to produce free hydroxyl radicals, this oxidative stress could still be limited by exploitation of features of pyruvate other than those already discussed. The mechanism is another feature that applicant contends is unique to pyruvate. It has been recognized that the cytotoxicity of oxygen-derived free radicals includes oxidation of labile —SH groups. Optimum functioning of vital enzymes such as $Na^+/K^+$-ATPase and glyceraldehyde-3-phosphate dehydrogenase or metabolite transporters (e.g., the specific mitochondrial pyruvate transporter) appears to depend on such labile —SH groups; other effects of the free radicals include the relatively unspecific peroxidation of membrane lipids which is thought to disturb normal membrane function; possibly, free radicals can also oxidize protein-thiols thus causing direct damage to structural proteins of the cytoskeletal apparatus [17] which can jeopardize the physical integrity and sturdiness of the cell.

Applicant proposes that pyruvate has the potential to strengthen the intrinsic cellular tolerance against this type of oxidative stress on labile but essential —SH groups. This latter mechanism probably operates via the well-known pyruvate-induced citrate accumulation; citrate is an allosteric inhibitor of phosphofructokinase, the main enzyme regulating glycolytic flux. Inhibition of phosphofructokinase leads to an accumulation of glucose-6-phosphate (G-6-P), the immediate phosphorylation product of glucose (hexokinase). G-6-P is also the substrate of the G-6-P dehydrogenase, the first and rate-limiting enzyme controlling the metabolic throughput of the pentose phosphate cycle; it has been shown that increased levels of G-6-P increase the rate of the pentose phosphate pathway in the heart [12]. This metabolic pathway produces reducing equivalents in the form of $NADPH_2$ which are normally used for reductive syntheses and, importantly, also to keep the glutathione system in its physiologic reduced state. The glutathione system is considered the main cellular defense against sudden oxidative stress due to oxygen-derived and possibly other free radicals. Thus, applicant points out that pyruvate, via an allosteric effect on glycolysis at the level of phosphofructokinase, has the potential to strengthen the reductive capacity of the glutathione system, which will likely improve cellular tolerance to acute oxidative stress. Of significance in this context is that reduced glutathione (GSH) likely prevents/minimizes oxidation of labile protein-SH groups; maintenance of the cellular GSH/GSSG redox status is therefore likely important for maintaining protein-thiols and enzyme-thiols in their physiologic reduced state. Several powerful enzymes that are instrumental for normal cell function contain labile —SH groups; known examples are the $Ca^{++}$-ATPase of the sarcoplasmic reticulum (excitation-contraction coupling in heart, skeletal and smooth muscle), the creatine kinase (maintaining the cytoplasmic phosphorylation potential in heart, skeletal and smooth muscle and brain), glycogen phosphorylase (mobilization of liver and kidney glycogen to stabilize blood glucose levels), and the already mentioned $Na+/K+$-ATPase (ubiquitous cellular $Na^+/K^+$ homeostasis, affecting also that of calcium via the $Na^+/Ca^{2++}$- and $Na^+/H^+$-exchangers) (for review see ref. [11]). Disabling these enzymes by oxidizing their labile —SH groups is incompatible with long-term cellular survival, not to mention the maintenance of their vital cell- and organ specific functions.

8) Non-enzymatic interaction of pyruvate with hydrogen peroxide: Another novel feature of pyruvate that applicant considers is its capacity to directly neutralize hydrogen peroxide on a 1 to 1 molar basis. Under cellular conditions this interaction is spontaneous and does not require enzyme catalysis; it is an interaction between pyruvate's carbonyl group (alpha-keto group) and hydrogen peroxide yielding carbon dioxide and acetate. This reaction is probably enhanced by the presence of free Fe2 + (ferrous Ion). The released carbon dioxide is highly diffusible across all cellular membranes and can thus immediately be washed out from cells, organs or removed from the body via the lung; acetate, the other product of the pyruvate-hydrogen peroxide interaction, can be readily activated by mitochondrial acyl-coenzyme A synthases yielding acetyl-CoA, the main substrate for the citric acid cycle. Applicant points out that this non-enzymatic mechanism of $H_2O_2$-pyruvate interaction could conceivably mitigate the sudden oxidative stress experienced by cells/organs previously compromised by lack of oxygen, lack of circulation, metabolic acidosis, iron overload, extreme metabolic stress.

9) Effect on blood oxygen transport: Pyruvate has also advantageous effects on blood, erythrocytes and their capacity to release oxygen at the specific oxygen tension in the microcirculation. It is well established that pyruvate can increase erythrocyte 2,3-diphosphoglycerate (2,3-DPG) levels [13]; 2,3-DPG is important for the position of the oxygen dissociation curve and hence the release of oxygen from hemoglobin at the partial pressures of oxygen prevailing in the microcirculation. This effect of pyruvate will likely improve the oxygen supply to parenchymal cells; the effect may become especially important in situations where oxygen supply is precarious. This effect of pyruvate requires the presence of adenine or inosine as well as relatively high concentrations of phosphate as additional substrates. The feature has been exploited in blood banking for decades, but applicant points out that this is an additional important argument for novel systemic pyruvate applications in conditions of oxygen deficiencies such as restriction of circulation (ischemia), high altitude (hypoxia), hemodilution (severe external or internal blood loss), severe anemia. However, under high altitude conditions, respiratory alkalosis may develop; if such a conditions exists, pyruvate application may not be justified, since it could aggravate the alkalosis, an effect that may offset the beneficial effect of 2,3-DPG accumulation on the oxygen dissociation curve.

SUMMARY OF THE INVENTION

It is the object of this invention to provide a pharmaceutical composition which contains as an active phosphorylation potential enhancing substance an alpha-ketocarboxylic acid compound or a pharmaceutically-acceptable salt thereof in an amount sufficient to prevent the deterioration or promote the restoration and preservation of normal cell functions.

DETAILED DESCRIPTION OF THE INVENTION

A. biological activity has been discovered for a pharmaceutical composition whose dominate function is to enhance the phosphorylation potential and to reduce hydrogen load within the cell thereby preventing the deterioration or promoting the restoration and preservation of normal cell functions. More precisely, applicant has discovered a pharmaceutical composition with the following nineteen(19) attendant itemized features:

FEATURES

1. A pharmaceutical composition comprising as an active phosphorylation potential enhancing substance an alphaketocarboxylic acid compound of the formula R—C(O)(CO)OH or a pharmaceutically-acceptable salt thereof in an amount sufficient to prevent the deterioration or promote the restoration and preservation of normal cell functions wherein R is alkyl of 1 to 12 carbon atoms; substituted alkyl of 1 to 12 carbon atoms, cycloalkyl of 3 to 10 carbon atoms, carboxyalkylene of 1 to 20 carbon atoms within the alkylene chain), halogen amino, alkylamino of 1 to 4 carbon atoms, dialkylamino of 1 to 4 carbon atoms in each alkyl group or phenyl); alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthtyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, or pyridyl; thienyl, indolyl, furyl; acridyl; quinolyl; piperadine; or pyridazinyl.

2. A composition of Feature 1 wherein R is an alkyl substituent selected from the group consisting of methyl, ethyl and prophyl.

3. A composition of Feature 2 wherein R is methyl.

4. A composition of Feature 1 wherein R is a carboxyalkyl selected from the group consisting of methyl, ethyl and prophyl.

5. A pharmaceutical composition according to Feature 1 which contains a parenteral fluid selected from the group comprising total parentheral nutritional fluids; kidney and peritoneal dialyses fluids; volume and plasma expanding fluids; pyruvate/acetate near-isotonic solutions; lactate/acetate-free pyruvate isotonic solutions; normal saline solutions; hemoglobin-substitute containing solutions; vitamin supplement product; and cardioplegic solutions.

6. An oral fluid for rehydration with electrolyte balances or rehydration without electrolyte balances comprising a pharmaceutical composition according to Feature 1.

7. A topical composition selected from the group comprising medicinal soaps; medicinal shampoos; sunscreens; medicinal ointments; dentifrice; mouthwash; douche solutions; and medicinal baths comprising a pharmaceutical composition according to Feature 1.

8. An intramuscular injectate selected from the group comprising an antibiotic and antiphlogistic comprising a pharmaceutical composition according to Feature 1.

9. A method of using the injectate of Feature 6 to treat local skin disorders.

10. An aerosolized composition comprising a composition according to Feature 1 or in combination with a bronchodilating agent.

11. A method of using the composition of Feature 10 to ameliorate or prevent the onset of abnormal conditions caused by a reactive airway disease.

12. A method according to Feature 11 wherein the airway disease is selected from the group consisting essentially of asthma and bronchopulmonary dyplasia.

13. A method of using the composition of Feature 1 as perfusion solution for isolated animal organs comprising the heart, liver, kidney, brain, spleen, vessels, arteries, endothelium, pancreas and glands.

14. A method of using the composition of Feature 1 as an incubation solution for bacterial or viral cells in culture or cloning studies.

15. A food product capable of enhancing physical endurance or providing refreshment comprising a pharmaceutical composition of Feature 1.

16. A food product according to Feature 15 wherein said product is a beverage drink.

17. A food product according to Feature 15 wherein said product is a confectionery food.

18. A food product according to Feature 17 wherein said product is selected for the group comprising candies or pastries.

19. A vitamin supplement product according to Feature 5 wherein said food product is a vitamin capsule containing thiamine (B1).

EXAMPLES

The herein offered examples of compositions provide methods for illustrating without implied limitation, formulations contemplated within the scope of this invention for activating the phosphorylation potential of cells.

The representative compositions are exemplary in nature to illustrate these compositions within the scope of this invention.

All temperatures not otherwise indicated are in degrees celsius (°C.) and parts of percentages are given by weight.

A: intravenous solutions

Example (1): i.v. Ringer's lactate augmented with pyruvate (near-isotonic):

per 100 ml solution:

600 mg sodium chloride USP 30 mg potassium chloride USP 310 mg sodium lactate 310 mg sodium pyruvate 20 mg calcium chloride USP pH 6.5 (6.0–7.5)

lactate 28 mEq/l pyruvate 28 mEq/l osmolarity about 300 mOsmol/l (calculated)

purified (quartz-double-distilled and sterilized) water

Example (2): i.v. lactate-/acetate-free Ringer's fortified with pyruvate (isotonic):

per 100 ml solution:

600 mg sodium chloride USP 30 mg potassium chloride USP 310 mg sodium pyruvate 20 mg calcium chloride USP pH 6.5 (6.0–7.5)

osmolarity about 273 mOsmol/l (calculated)

purified (quartz-double-distilled and sterilized) water

Example (3): i.v. 5% Dextrose solution fortified with pyruvate (hypertonic):

per 100 ml solution:

5 g Dextrose hydrous USP 287 mg sodium chloride USP 310 mg sodium pyruvate pH 4 (3.5–6.5)

hypertonic osmolarity about 406 mOsmol/l (calculated)

purified (quartz-double-distilled and sterilized) water

Example (4): i.v. 5% Dextrose in water fortified with pyruvate (isotonic):

per 100 ml solution:

5 g Dextrose hydrous USP 310 mg sodium pyruvate pH 4 (3.5–6.5)

hypertonic osmolarity about 280 mOsmol/l (calculated)

purified (quartz-double-distilled and sterilized) water

Example (5): i.v 0.45% sodium chloride solution fortified with pyruvate (hypotonic):

per 100 ml solution:

450 mg sodium chloride USP 310 mg sodium pyruvate pH 4 (3.5–6.5)

hypotonic osmolarity about 182 mOsmol/l (calculated)

purified (quartz-double-distilled and sterilized) water

B: Peritoneal Dialysis (PD) solutions

Example (5): PD solution fortified with pyruvate (isotonic):

final concentrations in dialysate:

sodium 132 mEq/l calcium 2 mEq/l magnesium 1.0 mEq/l chloride 105 mEq/l pyruvate 30 mEq/l Example (6): PD solution fortified with pyruvate and 1–4% dextrose (slightly hypertonic):

final concentrations in dialysate:

sodium 132 mEq/l calcium 2 mEq/l magnesium 1.0 mEq/l chloride 105 mEq/l pyruvate 30 mEq/l glucose (Dextrose) 1–4 g/100 ml C: Hemodialysis (HD) solutions Concentrations of anions and cations similar to PD solutions, fortified with sodium pyruvate and glucose D: Cardioplegic solutions Example (7): University of Wisconsin solution augmented with pyruvate (near-isotonic):

solution contains high potassium (30 mEq/l)

all major extracellular electrolytes in normal concentrations plus 1 mmol/l adenosine 5 mmol/l pyruvate pH adjusted to 7.4 equilibrated with 95% oxygen/5% carbon dioxide purified (quartz-double-distilled and sterilized) water E: Oral Rehydration Example (8): for an oral rehydration fluid augmented with pyruvate:

(modified world health organization (WHO) solution)

glucose 2 g/dl pyruvate sodium salt 1 g/dl sodium 90 mEq/l potassium 20 mEq/l chloride 80 mEq/l bicarbonate 30 mEq/l F. Oil/Water Ointment Example (9): for a universal oil/water ointment augmented with pyruvate:

calcium citrate 0.05 g sodium alginate 3.00 g

Methylparaben 0.20 g

Glycerin 45.00 g sodium pyruvate 0.05 g*

*=use pyruvic acid, if pH is alkaline double distilled water to make 100.00 g pH not known, probably about 6.0

G. Emulsifiable Ointment

Example (10): for a water-removable, emulsifiable ointment augmented with pyruvate:

polyethylene glycol 4000 50.0 g polyethylene glycol 400 40.0 g

Sorbitan Monapalmitate (Span 40(Atlas)) 1.0 g sodium pyruvate 0.05 g *

*=use pyruvic acid, if relatively low pH is desired double distilled water 9.0 g pH not known, probably about 6.0

H. Injectable Antibiotic

Example (11): for an injectable antibiotic augmented with pyruvate ceftriaxone sodium (Rocephin) 250 mg water 0.9 ml sodium pyruvate (final conc 4.5 mmol/l) 0.5 mg vial should contain these ingredients and should then be reconstituted with water

I. Medicinal Aerosol

Example (12): for a Medicinal aerosol for relief of asthma, augmented with pyruvate particle size 3 to 6 micron water/ethanol 1/1 by volume epinephrine HCl or isoproterenol HCl sodium pyruvate to final concentration of 0.5 mg/ml propellant 3 to 15%

J. Scientific Perfusion Solution

A method of using the composition of Feature 1 as scientific perfusion solution for isolated animal organs comprising the heart, liver, kidney, brain, spleen, any vessel, pancreas and other endocrine glands.

Example (13): for a modified Krebs-Henseleit solution augmented with pyruvate sodium chloride 116 mmol/l sodium bicarbonate 26 mmol/l potassium chloride 3.5 mmol/l potassium dihydrogen phosphate 1.2 mmol/l calcium chloride 1.0 mmol/l magnesium sulfate 0.6 mmol/l glucose (dextrose) 5.0 mmol/l sodium pyruvate 5.0 mmol/l solution equilibrated with Oxygen/Carbon dioxide=95%/5% temperature 37 Celsius pH 7.4–7.45 osmolarity 280 mosmol/l double distilled water must be used

K. Scientific Incubation Medium

A method of using the composition of claim 1 as scientific incubation medium for cells isolated from heart, liver, kidney, brain, spleen, any vessel, endothelium, pancreas and other endocrine glands.

Example (14): for a electrolyte incubation solution augmented with pyruvate sodium chloride 116 mmol/l sodium bicarbonate 26 mmol/l potassium chloride 3.5 mmol/l potassium dihydrogen phosphate 1.2 mmol/l calcium chloride 1.0 mmol/l magnesium sulfate 0.6 mmol/l glucose (dextrose) 5.0 mmol/l sodium pyruvate 5.0 mmol/l solution equilibrated with Oxygen/Carbon dioxide=95%/5% temperature 37 Celsius pH 7.4–7.45 osmolarity 280 mosmol/l

Albumin, essential amino acids, trace amounts of ferrous ion and copper salts and vitamins will have to be added to prevent growth limitation due to lack of essential nutrients and minerals. Antibiotics may have to be used to prevent unwanted bacterial growth. Osmolarity increases due addition of aminoacids and vitamins will be balanced by appropriate iso-osmolar reductions in sodium chloride.

L. Scientific Cloning Medium

A method of using the composition of claim 1 as incubation medium for cells used in scientific cloning studies or as a superfusing solution of cells plated on Petri dishes or seeded on latex particles.

Example (15): for a cloning/superfusing solution augmented with pyruvate sodium chloride 116 mmol/l sodium bicarbonate 26 mmol/l potassium chloride 3.5 mmol/l potassium dihydrogen phosphate 1.2 mmol/l calcium chloride 1.0 mmol/l magnesium sulfate 0.6 mmol/l glucose (dextrose) 5.0 mmol/l sodium pyruvate 5.0 mmol/l solution equilibrated with Oxygen/Carbon dioxide=95%/5% temperature 37 Celsius pH 7.4–7.45 osmolarity 280 mosmol/l

Albumin, essential amino acids, ferrous ion and copper salts and vitamins will have to be added to prevent growth limitation due to lack of essential nutrients and minerals. Antibiotics may have to be used to prevent unwanted bacterial growth. Osmolarity increases due addition of aminoacids and vitamins will be balanced by appropriate iso-osmolar reductions in sodium chloride.

M. Diagnostic Agar Culture Media

Example (16): for a method of using the composition of Feature 1 as diagnostic agar or culture media for bacterial growth.

Agar or culture media will be fortified with 5 mM glucose plus 5 mM sodium pyruvate.

N. Metabolic Acidosis

Example (17): for a clinical method of reducing or ameliorating the level of metabolic acidosis in a patient using an effective dose of the composition of claim 1.

Use of an i.v. solution fortified with pyruvate; examples are given in Feature 3, "intravenous solutions".

O. Preventing or Reducing Formation of Hydrogen Peroxide-Dependent Formation of toxic free radicals Example (18): for a clinical method of preventing or reducing the formation of hydrogen peroxide -dependent formation of toxic free radicals (superoxide anion, hydroxyl radical) in a patient recovering from an ischemic insult (stroke, thrombosis, myocardial infarct) using an effective dose or infusion of the composition of Feature 1.

Use of an i.v. solution fortified with pyruvate; examples are given in Feature 3, "intravenous solutions".

P. Refreshments and Energizing Drinks

Commercial refreshments and energizing drinks usually contain sugar, protein, fat and a number of essential vitamins and minerals.

Example (19): meal replacement drink (milk-shake-type):

A 12 Fl OZ (355 ml) can containing additional 200 mg sodium pyruvate ( about 5 mmol/l)

Example (20): thirst quencher drink which does not contain fat and protein( Gatorade-type):

A 32 Fl OZ (946 ml) bottle containing additional 533 mg sodium pyruvate (about 5 mmol/l)

Example (21): nutritional water-soluble energizing powder which does not contain fat and protein:

A 21 OZ (6 g) bag (for 6 OZ (178 ml) water) containing additional 825 mg sodium pyruvate (about 7.4 mmol/178 ml=42 mmol/l)

with the following standard ingredients:

vitamin C 2000 mg, potassium 400 mg, sodium 120 mg, calcium 100 mg, magnesium 40 mg, manganese 3 mg, zinc-ascorbate 4 mg, chromium-picolinate-ascorbate 20 micro g, vitamin B1 0.75 mg, vitamin B2 0.85 mg, niacin-niacinamide 10 mg, vitamin B6 20 mg, vitamin B12 50 mg, panthothenic acid 5 mg. Fructose (better glucose) as a sweetener in a base of citric, tartaric, aspartic, and malic acid. Lemon flavors added plus potassium phosphate to adjust pH to near normal.

Q. Cereal Bars and Freeze-Dried Food Products

Commercial cereal bars and freeze-dried food products often contain complex carbohydrates, simple sugars, protein, saturated and unsaturated fats and a number of essential vitamins and minerals as well.

Example (22): breakfast replacement bar (cereal-type):
A 40 g bar containing additional
  5.5 g sodium pyruvate (about 50 mmol)

Example (23): freeze-dried action food for endurance hikers and military in the field:
A 100 g bag containing additional
  14 g sodium pyruvate (about 126 mmol)

R. Vitamin Capsules

Commercial vitamin capsules are widely available. Especially vitamin B1, thiamine, is absolutely essential for oxidative decarboxylation of pyruvate by pyruvate dehydrogenase in mammalian as well as yeast cells (alcoholic fermentation). Thus, for a composition according to Feature 1 to work efficiently, the water-soluble vitamin B1 must be present in sufficient concentrations. To enhance the effect of Feature 1 compositions, pyruvate and congeners will be combined with thiamine preparations. Accordingly applicant contemplates the use of Pyruvated capsules that contain vitamin B1 or a multi vitamin B system where thiamine is a main constituent.

Example (24): pyruvated vitamin B1:
A capsule containing 250 mg vitamin B plus additional
  550 mg sodium pyruvate (about 5 mmol)

Example (25): pyruvated vitamin B complex:
A capsule containing all major vitamin B's plus additional
  550 mg sodium pyruvate (about 5 mmol)

S. Dentrifice Products

Pyruvate added to tooth pastes may help roborize the gingiva, especially when suffering from gingivitis or other tooth-decaying diseases. Accordingly tooth pastes enhanced with compositions according to Feature 1 are claimed.

Example (26): pyruvated tooth paste without vitamin B:
A tooth paste, 5 g, containing additional
  550 mg sodium pyruvate (about 5 mmol)

Example (27): pyruvated tooth paste with vitamin B 1:
A tooth paste, 5 g, containing 250 mg vitamin B 1 plus additional
  550 mg sodium pyruvate (about 5 mmol)

T. Hair Products

Hair shampoos containing pyruvate compositions may strengthen hair health and growth by roborizing the hair follicles. A shampoo fortified by pyruvate is claimed.

Example (28): pyruvated hair shampoo without vitamin B1:
A hair shampoo, 5 g, containing additional
  550 mg sodium pyruvate (about 5 mmol)

Example (29): pyruvated hair shampoo with vitamin B 1:
A hair shampoo, 5 g, containing 250 mg vitamin B 1 plus additional
  550 mg sodium pyruvate (about 5 mmol)

The above-mentioned compositions illustrate the advantageous use of pyruvate over presently known agent where pyruvate applications/supplementations/substitutions appear to be superior to or could markedly enhance current practices and clinical routines.

VII. CONTEMPLATED CLINICAL APPLICATIONS FOR PYRUVATE

A. ADVANTAGES OVER PRESENTLY KNOWN AGENTS

1) Cardiac ischemia/reperfusion damage, heart transplantation, and cardiopulmonary bypass: Pyruvate improves and accelerates recovery of cellular phosphorylation potential and ventricular function and inotropic state. In contrast, traditional clinical lactate/glucose drips (infusions) are either without effect or likely even damaging to the phosphorylation potential and reperfusion function; this is the case because the recovering but still damaged cell needs to release, not take up, lactate in an effort to remove intracellular $H^+$ and to reduce the concentration of NADH. In the blood-perfused heart in situ, for example, a net release of lactate is usually a sign of hypoxia, ischemia, extreme metabolic stress. Thus, infusing lactate into an organ that is attempting to remove its own endogenous lactate waste is clearly not optimal.

With regard to acetate, this compound is known to lower the phosphorylation potential in experimental hearts and has also been found to impair reperfusion recovery in experimental situations. As for clinical solutions containing aspartate or glutamate, both of which have been reported to be beneficial under some conditions, their mechanism is far from understood or proven; in particular, there are no known well characterized transporters on the plasma membrane that would allow efficient movement of these highly polar dicarboxylates into the cell. In contrast, there is a high-capacity monocarboxylate transport system for pyruvate (and lactate) which, at least in heart and liver, has the capacity to transport pyruvate into and out of the cell and the mitochondria at rates that are more than sufficient under most, if not all conditions in health and disease.

2) Post-surgical clinical stunned myocardium: Pyruvate likely improves the prolonged dysfunction and low-contractility state of the postischemic ventricle via enhancing the phosphorylation potential and possibly via removing intracellular $H^+$. Also the specific anaplerotic (replenishing) effect on mitochondrial malate and oxaloacetate pools can only be considered desirable for the stunned myocardium. Pyruvate, unlike the clinically used adenosine (University of Wisconsin solution has 1 mM adenosine; adenosine is routinely injected to treat supraventricular tachycardia and other forms of arrhythmias), has no known serious hypotensive or bradycardic effects; pyruvate unlike adenosine is not a potent vasodilator and hence does not dangerously lower peripheral resistance of the circulation. Adenosine, in contrast to pyruvate, does not replenish the crucial mitochondrial metabolite pools. Pyruvate, in contrast to the clinically widely used inotropic "support" by adrenergic agonists (epinephrine, dobutamine) or vagus blockade by atropine, is not forcing restoration of postischemic function at low-ischemic phosphorylation potentials. Experimental data from guinea pigs and pigs show that norepinephrine, calcium-agonists (BayK 8644), hypercalcemia, and dobutamine as well, all normalize reperfusion function of the stunned heart, but this improvement consistently occurs without restoration or enhancement of the phosphorylation potential, which is in marked contrast to pyruvate therapy. In guinea pig myocardium reperfused after a 45 min low-flow ischemia, these traditional inotropic interventions restored function only at the expense of the cytoplasmic phosphorylation potential.

Pyruvate can thus be seen as a novel class of inotropes, the metabolic inotropes, which produce a gentle and yet robust improvement of postischemic function, and that as permitted by or in accordance with the real-time cellular energy state. This is the principal difference with respect to current clinical adrenergic (inotropic) drug routines which force normalization of function of the damaged and/or disease-weakened heart (which, without the drugs, would be in a state of hemodynamic failure or stunning); but these inotropic regimens do not reenergize the cells nor do they create an anabolic situation to replenish crucial myocardial metabolite pools depleted by the prior damaging stimuli. Such forced restoration of performance can therefore occur at a potentially dangerous cost, a deleterious change in key metabolite levels resulting in a further fall in cellular energy level (phosphorylation potential); this will likely have obligatory but adverse consequences in cellular sodium homeostasis and calcium handling, which eventually likely combine to accelerate the development of acute and complete, and perhaps also essentially irreversible failure.

Current clinical "inotropic support" for postoperative cardiac patients (who usually have aged-or pre-damaged/ weak hearts which probably function already at below-physiologic phosphorylation potentials) is essentially only a symptomatic or "cosmetic" treatment of ventricular function, without appropriate concern for correcting the underlying cause of the precarious energy balance and/or the associated $Na^+$ and $Ca^{2+}$ ionic imbalances and/or the reduced $Ca^{2+}$ sensitivities of the excitation-contraction process. Indeed, adrenergic agonists have long been recognized to lower the $Ca^{2+}$-sensitivity of the myofilaments in the myocardium, a situation which makes it virtually impossible to rationalize the use of adrenergic support in stunned heart, as stunning is typically associated with exactly this type of reduced calcium sensitivity at the myofilament level [14–16]. It comes therefore as no surprise that many cardiac surgeons view customary inotropic drug regimens, when applied to the stunned or spontaneously failing human heart, with concern and skepticism.

Pathophysiologically it is important to understand that inotropic drug therapy in the cardiac patient shifts the energy demand/supply balance toward higher demand; in aged hearts this may well occur in the presence of preexisting energy depletion/ion imbalance and/or a compromised coronary circulation (chronic ischemic coronary disease of the aged heart). This could put more myocytes at risk, at a moment when their recovery process has not yet begun or not yet been completed. In marked contrast, pyruvate metabolic inotrope therapy shifts the energy demand/supply balance in favor of larger supply; the ensuing functional improvements are spontaneous, a natural consequence of improved cellular energy status, redox status, and ion homeostasis; all subsequent improvements of function are fully commensurate with and supported by the existing intrinsic energy supply status of the heart.

Again, adrenergic inotropic drugs can cause desensitization towards calcium of the contractile elements, a shift toward the left in the tension/$pCa^{++}$ curve of the contractile elements [14]; myocardial stunning also is often associated with a similar calcium desensitization [15, 16]. Consequently, it would not seem justified to continue the practice of indiscriminate use of adrenergic inotropic "support" in the post-surgical cardiac patient with the stunned heart syndrome. Pyruvate as a metabolic inotrope would seem the more appropriate choice, even if it were only used in combination with classical adrenergic support in order to reduce the requisite dose of adrenergic agents.

3) Metabolic acidosis: The unique and special aspects of cellular pyruvate-$H^+$ symport and metabolic pathways will help lower the size of the intracellular $H^+$ ion pool. Since all vital organs have substantial amounts of pyruvate transporters, lactate and pyruvate dehydrogenases and also mitochondria, pyruvate can be expected to counteract cellular acidosis body-wide, especially in heart, liver, lung, kidney, brain, and skeletal muscle. This anti-acidotic effect of exogenous pyruvate principally occurs according to the following mechanism: when one pyruvate anion enters the cell, it will be obligatorily accompanied by one hydrogen ion; this hydrogen ion will then be used in the lactate dehydrogenase reaction to form the lactate anion (without $H^+$); the lactate anion will then be exported from the cell together with one hydrogen ion; this latter hydrogen ion comes of course from the global cellular hydrogen ion pool, thus reducing cellular acidification. The net effect is removal of one intracellular hydrogen ion per one pyruvate taken up and reduced to lactate or oxidized to carbon dioxide and water.

Conversely, lactate infusion is contraindicated during systemic metabolic acidosis because lactate is a metabolic waste product under these conditions and produces rather than removes intracellular hydrogen ions. The mechanism is as follows: when one molecule of lactate enters the cell, it takes one hydrogen ion with it (much as pyruvate); then lactate will be oxidized to pyruvate generating rather than consuming another intracellular hydrogen ion (lactate dehydrogenase reaction). Thus, lactate oxidation to pyruvate via lactate dehydrogenase generates cytoplasmic hydrogen ions, whereas pyruvate reduction to lactate by reversal of lactate dehydrogenase removes cytoplasmic hydrogen ions. Lactate infusion can therefore only exacerbate a preexisting cellular acidosis, while pyruvate infusion will likely ameliorate it. This beneficial effect of pyruvate can be established of course only when there is some residual organ/cellular perfusion.

4) Diabetic ketoacidosis and/or coma: Pyruvate infusion will ameliorate the metabolic acidosis as explained. Pyruvate will also directly improve cellular oxidative carbohydrate metabolism. The pyruvate dehydrogenase is inhibited in ketosis due to the high blood concentration of beta-hydroxybutyrate [17]. This mitochondrial enzyme inhibition can be overcome simply by raising blood pyruvate concentration, the mechanism being the allosteric effect of pyruvate on PDH phosphorylation as explained above.

Pyruvate infusion during diabetic ketosis will not have the complications of insulin therapy: 1) Pyruvate's half live in blood is on the order of minutes, i.e. much shorter than that of insulin (order of ½ to 1 hour), as virtually all organs readily metabolize pyruvate. 2) Pyruvate will also not drastically lower blood sugar levels, as the glucose transport per se into skeletal and heart muscle as well as liver and kidney is not stimulated or inhibited directly by pyruvate. 3) Thus, dangerous hypoglycemia will not be a complication of systemic pyruvate administration to keto-acidotic diabetics.

Alternatively, if insulin treatment proves indispensable for some keto-acidotic or comatose patients, it would appear that the dose of insulin could be lowered by co-application of sufficient pyruvate. Thus pyruvate has the potential to substantially lower the dose and hence the risks of acute insulin administration during emergency medical care situations involving the diabetic patient.

5) Hypovolemic shock (auto accident, combat casualty, extensive internal or external bleeding): Hypovolemic shock is often associated with or progresses to systemic metabolic acidosis and a general deenergization of all organs; this will eventually lead to multiple organ failure and hardly manageable end-stage situations. Pyruvate as a natural alkalinizer that simultaneously enhances recovery of. rephosphorylation of the cell and stabilizes the physiologic reduced state of vital —SH enzymes and transporters, can be expected to be much more effective than the traditional glucose, gluconate, lactate, or calcium drips alone. Combined with human full blood, pyruvate supplementation can be expected to enhance all known parenteral drip regimens.

6) Cardiogenic shock: The acutely or chronically failing heart is likely deenergized (low phosphorylation potential) and pyruvate metabolic inotrope therapy has the potential to bring about and/or expedite recovery from failure by reestablishing the cytoplasmic phosphorylation potential, the ion homeostasis and by mitigating any existing residual acidosis.

7) Other forms of shock: Anaphylactic shock, endotoxin shock. Pyruvate is an ideal agent to improve oxidative energy and hydrogen metabolism of the heart and all major organs that contain lactate dehydrogenase and more than trace amounts of mitochondrial pyruvate dehydrogenase/carboxylase (heart, brain, lung, liver, kidney, skeletal muscle, smooth muscle).

8) Hemosiderosis: Pyruvate could be beneficial here too because it would be expected to possibly reduce the concentration of free iron in the cells; this can take place because pyruvate would reduce the concentration of $[NADH]^*[H^+]$ which would attenuate, if not completely blunt the already mentioned reductive release of iron from binding sites such as ferritin, haem-protein or myoglobin. Consequently, the damaging Fenton-type reactions could possibly be attenuated thus reducing the chronic overall cellular damage by toxic oxygen-derived free radicals.

9) Strenuous exercise, physical exertion, endurance: Probably skeletal muscle and heart in particular, but perhaps also other organs, suffer from energetic exhaustion (low phosphorylation potential) due to prolonged strenuous/excessive physical stress. Such a condition appears to be ideal for application of pyruvate metabolic inotropic therapy, since restoration of the phosphorylation potential and anaplerotic replenishment of key mitochondrial metabolites would be expedited and is of primary concern in such conditions. Pyruvate, by effectively competing with lactate for transport into heart, liver, skeletal muscle and likely other organs will additionally alleviate intracellular hydrogen load thus enhancing the recovery process.

10) Acute sickle cell crisis: Systemic hemolysis and local microembolism with subsequent ischemia are widespread. The resulting anemia could favorably respond to pyruvate because, when applied in combination with adenine or inosine (two degradation products of ATP), levels of 2,3-diphosphoglycerate would increase in the remainder but still intact red cells; such a mechanism will certainly improve oxygen delivery to the tissues suffering from acute anemia combined with multiple microembolism and microinfarctions. Thus, the need to immediately infuse donor blood or red cell concentrates with its associated problems (blood group incompatibilities) and risks of pathogens (e.g. hepatitis, AIDS) may well be reduced.

The other complication, multiple systemic and organ-wide microembolism, will also probably be responsive to pyruvate, because pyruvate reduces the complications of ischemia itself and also those of subsequent reperfusion (after dissolution/organization/recanalization of the microemboli) as discussed above.

11) Kidney dialysis (inpatient, outpatient, home) and peritoneal dialysis: Combat acidosis and maintain cells functional by optimizing energy status and hydrogen ions homeostasis in face of pathological concentrations of urea, creatinine, etc..

12) Organ preservation and transplantation: Immediately after organ harvesting an initial perfusion with pyruvate-containing salt solutions/plasma expanders/hemoglobin substitutes instead of current pyruvate-free solutions (to remove cellular elements and clotting factors) would be superior; this is the case because pyruvate would reduce the amount of intracellular NADH, raise the phosphorylation potential, and optimize cellular ionic homeostasis combined with a stabilization of the membrane potential. Also, since the procedures to collect and store donor organs usually create an ischemia/reperfusion-type condition which is typically followed by hypothermic storage and metabolic arrest, pyruvate therapy would be useful, since it is also directed at hydrogen peroxide-dependent hydroxyl radical damage. Further, during cold storage of the organs, the presence of high levels of pyruvate would further minimize gradual accumulation of reducing equivalents, which in turn would minimize the reductive release of ferritin $Fe^{2+}$ and hence reduce the probability of rewarming and reperfusion damage due to Fenton-type reactions. In this regard the currently often used University of Wisconsin-Solution and St. Thomas Solution could be enhanced by adding, e.g., 2–5 mM pyruvate.

13) Medical emergency resuscitation: Shock-like situations, hypotonia, blood loss, extensive burns and similar conditions can be expected to respond favorably to pyruvate metabolic and anaplerotic treatment. Quick reestablishments of cellular energy states, of crucial metabolite pools and transmembrane ion gradients, combined with gentle reduction of intracellular acidosis would be the main beneficial mechanisms. Conventional lactate or acetate containing solutions cannot effectively combat intracellular acidosis; adenosine containing solutions would be contraindicated because of the danger of adverse cardiovascular side effects. Pyruvate solutions would also avoid the potentially hazardous lowering of myocardial energy state that is likely to occur with catecholamine containing injectates. At the minimum, pyruvate therapy would promise to reduce the dosage of adrenergic inotropic drugs and also of bicarbonate and thus lower their potentially damaging side effects on cellular energetics and ionic homeostasis.

14) Status asthmaticus: Any bronchiolar smooth muscle spasm is prone to cause secondary lung ischemia and certainly ventilation/perfusion imbalances in the lung. This can lead to systemic hypoxemia and respiratory acidosis in severe cases. Current standard therapy is inhalation of aerosols usually containing a b-agonist such as albuterol or other congeners of isoproterenol, all of which are broncho dilators (smooth muscle relaxants). It seems possible that aerosolized pyruvate might also be efficacious, as pyruvate would help maintain the smooth muscle's metabolic phosphorylation potential and hence also its electrical membrane potential. The combined effect of these changes could favor bronchiolar relaxation (a complete relaxation of precontracted smooth muscle via this mechanism appears not impossible at this time, but remains purely speculative). Pyruvate could also be beneficial in combination therapies with albuterol, perhaps allowing the patient to inhale smaller amounts of adrenergic drugs at reduced frequency; the mechanism of such a pyruvate effect could again be the overall metabolic and energetic improvement of the bronchial smooth muscle.

B. PROBLEMS WHICH CAN BE SOLVED BY CLINICAL USE OF PYRUVATE

In principal, the clinical utility of pyruvate metabolic therapy is in the area of correcting cellular acidosis, hypoxia and ischemia prior to as well as during reperfusion, intracellular overload with reducing equivalents and $H^+$, mitochondrial metabolite exhaustion, and cytoplasmic energy deficiencies. Pyruvate restores faster than normal cellular energy state, ionic homeostasis, membrane potential; in consequence of these changes pyruvate will likely improve both the basal cellular functions and their organ-specific function; in addition there will likely be an improved metabolic status during cellular recovery from damage or during repair. With regard to the stunned heart muscle pyruvate is a metabolic inotrope without the problematic side effects of the traditional adrenergic or pharmacologic inotropes.

With regard to all cells and organs that contain mitochondria, pyruvate is also an anaplerotic agent, since it helps maintain crucial cytoplasmic and mitochondrial metabolites at levels required for maintenance of normal function and metabolic/functional reserves. This feature would seem to be important in situations during and after non-lethal, reversible injury. Pyruvate also acts as a natural antidote for hydrogen peroxide (and hence the formation of oxygen-derived free radicals) which can produce wide-spread intracellular and extracellular damage. Some major clinically relevant examples are presented in, but are not limited to those conditions discussed in section A 1) to A 14) above.

C. KNOWN AND POSSIBLE USES FOR PYRUVATE AND SIMILAR ALPHA-KETOACID CONGENERS

1) Antihypertensive
2) Examples of section A 1) to A 14)
3) Radiation overdose: since radiation often produces free radicals and is associated with generation of hydrogen peroxide (nuclear power plant accident, X-ray overdose, radiation sickness, space radiation) pyruvate therapy, topical or intravenous, may prove beneficial as adjunct to current well tried treatment regimens.
4) Incubation media and perfusion media in biomedical and agricultural research: here pyruvate acts as a metabolic stabilizer in studies with isolated cells, subcellular organelles, microorganism etc., especially when these systems depend on oxidative phosphorylation and could easily become unduly acidotic or subject to spontaneous free radical damage.
5) Blood banking: high concentrations of pyruvate combined with adenine, inosine, and phosphate can raise red cell 2,3-DPG and rejuvenate stored blood.
6) Antidote to hydrogen peroxide: in cases where iron-and $H_2O_2$-dependent Fenton-type reactions are involved (reperfusion oxygen free radical damage) pyruvate would be expected to reduce, if not completely abolish the formation of cytotoxic oxygen-derived free radicals.
7) Refreshments and commercial sport drinks: any type of refreshment could possibly be enhanced by the inclusion of pyruvate replacing currently used lactate, fructose, sucrose or other poorly metabolizable carbohydrates. Electrolyte-balanced drinks could very likely be enhanced by inclusion of pyruvate. Pyruvate used as an enhancement of oral rehydration therapy would also fall into this category.
8) Emergency fluids in submarines/airplanes/hot-air balloons/simulated high-altitude devices and decompression chambers/space flight and station: if a (sudden) drop in oxygen partial pressure occurs, readily available pyruvate drinks could improve the body's high altitude adaptation via stimulating 2,3-DPG synthesis in the red blood cells. This type of pyruvate drinks should probably also contain adenine and or inosine in appropriate amounts. There is a potential for acute flatulence, since the hydrochloric acid of the stomach will produce free pyruvic acid which may not be completely absorbed into the portal system; the intestinal bacterial flora will likely quickly convert pyruvate to water and carbon dioxide or alternatively perhaps decarboxylate it to acetate.
9) Cosmetics and dermatology: Any application that targets the skin aging process, skin turgor, finger nail appearance, hair follicle growth or and hair shininess, might be enhancable by inclusion of pyruvate as a natural cellular energizer. Eczema, seborrhoic conditions, and other chronic skin irritations may be amenable to topical pyruvate therapy (ointments, shampoos, lotions). Sunscreens could possibly also be improved by addition of pyruvate, since it could act to absorb UV rays (maximum absorbance is at a wavelength of 210 nm) simultaneous with its anti-free radical effect which could counteract UV ray induced premature skin aging. Perhaps even the incidence of skin cancer in populations with long-lasting exposure to sunlight and UV rays could be reduced by regular applications of ointments containing pyruvate as a supplement, if not as the main active ingredient.
9) Antiobesity Diets: Supplement to dietary food formulations.
10) Psychotic crises: Since the brain has substantial amounts of PDH and lactate dehydrogenase and because the blood-brain barrier may not be completely tight for pyruvate (nothing concrete is known about the latter issue), acute psychiatric disorders may be treatable by parenteral or better intrathecal application of pyruvate-enhanced solutions. Certainly, classical lactate containing solution are contraindicated, since a brain that is out of its fine-tuned electrical and transmitter balance would probably have one or multiple foci of neurons and/or supporting glia whose energetic and ionic status is abnormal. Such hypothetical foci would be the target of metabolic pyruvate treatment. Pyruvate applied intrathecally may also be considered in such situations.
11) Total parenteral nutrition (TPN): pyruvate appears a reasonable supplement to current TPN solutions, since it furthers replenishment of mitochondrial key metabolites, improves virtually universally cellular energy status, removes inhibition of carbohydrate utilization by allosterically relieving PDH inhibition caused by ketosis and high blood fatty acid concentrations.
12) Broncho-pulmonary dysplasia of the premature infant: The hyaline membranes impair alveolar oxygen diffusion and create a condition of systemic hypoxia; especially when this is combined with metabolic acidosis, then there are two conditions in which pyruvate therapy can be expected to be beneficial.
13) Disseminated intravascular coagulation: The consequences of the diffuse loss of blood, hypotonia, anemia, all can be expected to respond favorably to pyruvate treatment.

VIII. SUMMARY OF NOVEL FEATURES

The general aim is to improve both the basal status of a living cell or organ as well as its cell- or organ-specific functions without jeopardizing cellular energy status and without resorting to drugs that shift the energy demand/supply balance toward increased demand; the goal is to stabilize or if possible to enhance the cellular phosphorylation potential, ionic homeostasis acid-base status, and membrane potential, which automatically would normalize or restore normal cellular function. Another goal is to strengthen intrinsic defense against and tolerance towards sudden or chronic oxidative stress due to endogenously generated toxic free radicals due to reperfusion-type situations and radiation exposures; a further goal is to minimize accumulation of reducing equivalents during organ damage/ischemia, as the latter metabolites can inhibit glycolytic (non-oxidative) energy production, produce damage of mitochondrial function upon reperfusion and also trigger the dangerous cycle of reductive release of free $Fe^{2+}$ which ultimately leads to generation of toxic free radicals.

Thus, the major targets for biological/clinical pyruvate applications are: 1) the cytoplasmic phosphorylation potential, the parameter that ultimately controls ionic homeostasis and powers all endergonic processes (e.g., muscle contraction, sodium and calcium pumping in excitable and quiescent cells, sodium and water reabsorption in kidney, synthesis and transport of transmitters/hormones in brain, detoxification cycles in liver). 2) the obligatory stoichiometry between all known specific (phosphorylating) protein kinases and the [ATP]/[ADP] ratio; since the [ATP]/[ADP] ratio is a key component of the phosphorylation potential. $\{[ATP]/([ADP]*[P_i])\}$, it is likely that the potential is also involved in regulatory enzyme or protein phosphorylation and hence in fine-tuning processes such as control of cardiac contractility or calcium-sequestration by sarcoplasmic reticulum $Ca^{++}$ pump. 3) the cellular $NAD^+$/$NADH_2$ redox status; by keeping the cytoplasmic $[NAD^+]$/$[NADH_2]$ concentration ratio relatively oxidized during ischemia, which can be expected to minimize hazardous secondary effects of NADH accumulation on glycolysis mitochondrial energy coupling and reductive release of damaging $Fe^{2+}$. 4) the cellular GSH/GSSG redox status; by keeping the reductive potential of the glutathione system high, essential protein-SH, transporter-SH, and enzyme-SH groups can be better maintained in their physiologic reduced state during states of oxidative stress. 5) Strengthening and expediting the cellular metabolic recovery process, especially with regard to mitochondrial oxaloacetate. 6) Metabolic alkalization and removal of intracellular hydrogen ion loads. 7) Hydrogen peroxide, by direct interaction with pyruvate the peroxide is spontaneously degraded to biologically benign compounds instead of serving as precursor for the cytotoxic hydroxyl radical in Fenton-type reactions. 8) The red blood cells whose ability to release oxygen in the microcirculation can be improved by pyruvate via the 2,3-DPG mechanism.

Novel is here the focus on the phosphorylative, energetic, and reductive potential of the cell to correct a problem caused by pathological deenergization and/or acidification. Novel is the approach to use a metabolic intervention (by pyruvate) rather than customary clinical drug therapies. Novel is also that administration of pyruvate likely strengthens the intrinsic natural antioxidant defense, that pyruvate itself can act as a hydrogen peroxide antidote, that it "clamps" the cytoplasmic redox status thereby preventing excessive accumulation of reducing equivalents during ischemia, which subsequently could impair mitochondrial function and also induce the release of $Fe^{2+}$ thus initiating damaging Fenton-type reactions. This concept shifts the focus away from conventional symptomatic medical therapies to the treatment of the underlying biochemical and metabolic disorder (acidosis, deenergization, oxidative stress).

It is not the goal to obtain quick "cosmetic" improvements of organ function with disregard for the metabolic status of cells, organs or the entire body; such therapies, while often temporarily producing improved performance, often also produce further metabolic derangements of a system that was already in a preexisting precarious metabolic state. Experience has demonstrated that not rarely such therapies, after initial success, speed up ultimate cellular and organ failure.

The main principal goal is therefore to first improve the metabolic status of the system, then enhance the systems physiologic performance and that only as safely permitted and supported by the real-time cellular energetics.

IX. REFERENCES

1. Mallet R. T. et al. 1993: In: Interactive Phenomena in the Cardiac System, Sideman S., Beyar R. edts., Plenum Publishing Corp., in press
2. Nohl et al, Free Rad Res Comms 1993;18:127–137
3. Downey J. M. Annu Rev Physiol 1990;52:487–504
4. Paller M. S. et al. J Clin Invest 1984;74:1156–1164
5. Camporti M. Lab Invest 1985;53:599–623
6. Salahudeen A. K. et al. J Clin Invest 1991;88:1886–1893
7. Nicotera et al. Drug Metabolism Rev 1989;20; 193–201
8. Cohen G. 1985 In: Handbook of Methods for oxygen radical research. Greenwald R. A. edt., CRC Press, pp. 55–64
9. Funk et al. Eur J Biochem 1985; 152:167–172
10. Voogd A. et al. J Clin Invest 1992; 90:2050–2055
11. Reed D. J. Annu Rev Pharmacol Toxicol 1990;30:603–631
12. Zimmer H. G. et al. J Mol Cell Cardiol 1981;13:531–535
13. Duhm J Biochim Biophys Acta 1974;343:89–100
14. Holroyde M. I. et al. Biochim Biophys Acta 1979;586:63–69
15. Kusuoka H. et al. Circ Res 1990;66:, 1268–1276
16. Hofman P. A. et al. Circ Res 1993;72:50–56
17. Bringer R. et al. Eur J Physiol 1983;397;214–219

What is claimed is:

1. A method for enhancing the phosphorylation potential within the cells of a mammal in order to prevent the deterioration or promote the restoration and preservation of normal cell functions thereby enhancing physical endurance or refreshment comprising administering to a mammal in need thereof a food product containing a pharmaceutical composition having as an active ingredient thereof a salt of an alpha-ketocarboxylic acid having the formula R—C(O)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation.

2. The method in accordance with claim 1 wherein said food product is a beverage drink.

3. The method in accordance with claim 1 wherein said food product is a confectionery food.

4. The method in accordance with claim 3 wherein said food product is selected from the group comprising candies and pastries.

5. A food product for enhancing the phosphorylation potential within the cells of a mammal in order to prevent the deterioration or promote the restoration and preservation of normal cell functions thereby enhancing physical endurance or refreshment comprising a pharmaceutical composition having as an active ingredient thereof a salt of an alpha-ketocarboxylic acid having the formula R—C(O)(CO)OM wherein R is alkyl of 1 to 12 carbon atoms; substituted alkyl of 1 to 12 carbon atoms, cyloalkyl of 3 to 10 carbon atoms, alkenyl of 2 to 6 carbon atoms; alkynyl of 3 to 6 carbon atoms; benzyl; substituted benzyl (wherein the substituent is methyl, phenyl on the alpha carbon atom or the substituent is methyl, dimethyl, halo, dihalo, or ethoxy on the phenyl ring); adamantyl; phenyl; naphthyl; substituted phenyl or substituted napthyl (wherein the ring is mono-, di-, or trisubstituted and the substitutents are alkyl of 1 to 4 carbon atoms, halo, alkoxy of 1 to 4 carbon atoms, phenoxy, trihalomethyl, dimethylamino, diethylamino, and M is a cation.

6. The food product in accordance with claim 5 wherein said product is a beverage drink.

7. The food product in accordance with claim 5 wherein said food product is a confectionery food.

8. The food product in accordance with claim 5 wherein said food product is selected from the group comprising candies and pastries.

* * * * *